(12) United States Patent
Pellicer-Martinez et al.

(10) Patent No.: US 8,334,298 B2
(45) Date of Patent: Dec. 18, 2012

(54) TREATMENT OR PREVENTION OF OVARIAN HYPERSTIMULATION SYNDROME (OHSS) USING A DOPAMINE AGONIST

(75) Inventors: Antonio Pellicer-Martinez, Valencia (ES); Joan-Carles Arce, Dragor (DK); Carlos Simon-Valles, Valencia (ES); Raul Gomez-Gallego, Castellon de la Plana (ES)

(73) Assignee: Ferring International Center S.A., St. Prex (CH)

( * ) Notice: Subject to any disclaimer, the term of this patent is extended or adjusted under 35 U.S.C. 154(b) by 91 days.

(21) Appl. No.: 11/912,456

(22) PCT Filed: Apr. 24, 2006

(86) PCT No.: PCT/IB2006/000989
§ 371 (c)(1),
(2), (4) Date: May 28, 2008

(87) PCT Pub. No.: WO2006/117608
PCT Pub. Date: Nov. 9, 2006

(65) Prior Publication Data
US 2008/0293693 A1 Nov. 27, 2008

Related U.S. Application Data

(60) Provisional application No. 60/676,165, filed on Apr. 29, 2005.

(51) Int. Cl.
*A01N 43/42* (2006.01)
*A61K 31/44* (2006.01)
*C07D 221/06* (2006.01)
(52) U.S. Cl. ...................... 514/290; 546/110
(58) Field of Classification Search .................. 514/290; 546/110
See application file for complete search history.

(56) References Cited

U.S. PATENT DOCUMENTS

| | | |
|---|---|---|
| 4,565,818 A | 1/1986 | Nordmann et al. |
| 5,639,743 A | 6/1997 | Kaswan et al. |

FOREIGN PATENT DOCUMENTS

| | | |
|---|---|---|
| EP | 0077754 | 4/1983 |
| WO | 03/092595 | 11/2003 |
| WO | 2004/041164 | 5/2004 |

OTHER PUBLICATIONS

Schultz et. al., Pituitary, 2000, Kluwer Academic Press, vol. 3, pp. 239-249.*
Aboulghar et. al., Human Reproduction Update, 2003, European Society for Human Reproduction and Embryology, vol. 9, No. 3, pp. 275-289.*
McElhinney et. al., Bailliere's Clinical Obstetrics and Gynecology, 2000, Harcourt Publishers, vol. 14, No. 1, pp. 103-122.*
Al-Shawaf et. al., Best Practice and Research Clinical Obstetrics and Gynaecology, 2003, Elsevier, vol. 17, No. 2, pp. 249-261.*
Papaleo et al., "Cabergoline influences ovarian stimulation in hyperprolactinaemic patients with polycystic ovary syndrome," Human Reproduction 16(11):2263-6 (Nov. 2001).
Gomez et al., "Tyroxine hydroxylase (TH) downregulation in hyperstimulated ovaries reveals the dopamine agonist bromocriptine (Br2) as an effective and specific method to block increased vascular permeability (VP) in OHSS," Fertility and Sterility, (Sep. 2003) vol. 80, No. Sppl. 3, pp. S43-S44. print. Meeting Info: 59th Annual Meeting of the American Society for Reproductive Medicine, San Antonio, Texas, U.S.A., (Oct. 11-15, 2003) ("Gomez").
Morris et al., "Conservative management of ovarian hyperstimulation syndrome," J. Reprod. Med. 40(10):711-714 (Oct. 1995) ("Morris"); and.
Manno et al., "Cabergoline: a safe, easy, cheap, and effective drug for prevention/treatment of ovarian hyperstimulation syndrome?" Eur. J. Obstet. Gynecol. Reprod. Biol. 122(1):127-8 (Sep. 1, 2005) ("Manno").
Blankstein et al., "The Anovulatory Patient. An Orderly approact to evaluation and treatment" Infertility. 1988; 83: 97-102.
Derman et al., "Adverse Effects of Fertility Drugs" Drug Safety, (1994) 11/6 (408-421).
Gomez et al., "Vascular Endothelial Growth Factor Receptor-2 Activation Induces Vascular Permeability in Hyperstimulated Rats, and this Effect Is Prevented by Receptor Blockade" Endocrinology. 2002; 143, 4339-4348.
Murata et al., "Successful Pregnancy after Bromocriptine Therapy in an Anovulatory Women Complicated with Ovarian Hyperstimulation Caused by Follicle-Stimulating Hormone-Producing Plurihormonal Pituitary Microadenoma" The Journal of Clinical Endocrinology and Metabolism, 2003; 88(5): 1988-93.
Shimon et al., " Ovarian Hyperstimulation without Elevated Serum Estradiol Associated with Pure Follicle-Stimulating Hormone-Secreting Pituitary Adenoma" The Journal of Clinical Endocrinology and Metabolism, 2001; 86(8): 3635-40.
Smits et al., "Ovarian Hyperstimulation Syndrome Due to a Mutation in the Follicle-Stimulating Hormone Receptor" The New England Journal of Medicine, 2003, vol. 349:760-766.
Welter et al., "Regulation of the VEGF-System in the Endometrium during Steroid-Replacement and Early Pregnancy of Pigs" Exp Clin Endocrinol Diabetes. 2003; 111 (1): 33-40.
Basu et al., "The neurotransmitter dopamine inhibits angiogenesis induced by vascular permeability factor/vascular endothelial growth factor" Nature Medicine May 2001; 7 (5): 569-74.
Sarkar et al., "Dopamine in vivo inhibits VEGF-induced phosphorylation of VEGFR-2, MAPK, and focal adhesion kinase in endothelial cells" Am J Physiol Heart Circ Physiol. 2004; 287: H1554-60.
Tsunoda et al., "Treatment for ovarian hyperstimulation syndrome using an oral dopamine prodrug, docarpamine" Gynecol Endocrinol. 2003; 17: 281-286.

(Continued)

*Primary Examiner* — Sreeni Padmanabhan
*Assistant Examiner* — Sarah Pihonak
(74) *Attorney, Agent, or Firm* — Fish & Richardson P.C.

(57) ABSTRACT

Disclosed herein is a method for preventing ovarian hyperstimulation syndrome in a subject by administering an effective amount of a dopamine agonist in a pharmaceutically acceptable carrier. Also disclosed herein is a method for treating ovarian hyperstimulation syndrome by administering an effective amount of a dopamine agonist in a pharmaceutically acceptable carrier.

25 Claims, 2 Drawing Sheets

OTHER PUBLICATIONS

Gonen et al., "The Influence of Transient Hyperprolactinemia on Hormonal Parameters, Oocyte Recovery, and Fertilization Rates in in Vitro Fertilization" Journal of in vitro fertilization and embryo transfer: IVF, (Jun. 1989) 6 (3) 155-9.

Seppala et. al., "Suppression of prolactin secretion during ovarian hyperstimulation is followed by elevated serum levels of endometrial protein PP14 in the late luteal phase" Human reproduction (Oxford, England), (May 1989) 4 (4) 389-91.

Collins et al., "Human menopausal gonadotropin/human chorionic gonadotropin-induced ovarian hyperstimulation with transient hyperprolactinemia: steroidogenesis enhanced during bromocriptine therapy in monkeys" Journal of clinical endocrinology and metabolism, (Oct. 1984) 59 (4).

Aono, T., "Progress in Ovulation Induction" Asian Medical Journal (1997), 40 (7), 354-360.

Kauppila et al., "Hypoprolactinemia and ovarian function" Fertility and sterility, (Mar. 1988) 49 (3) 437-41.

Kamilova D.P. et al, Case of Severe Ovarian Hyperstimulation Syndrome, 1999 (D4) with English language translation of the relevant extracts.

Patent Office of The Russian Federation, Office Action (Inquiry) of the State Examination Dated Oct. 22, 2010 in English.

* cited by examiner

TREATMENT OR PREVENTION OF OVARIAN HYPERSTIMULATION SYNDROME (OHSS) USING A DOPAMINE AGONIST

CROSS-REFERENCE TO RELATED APPLICATIONS

This application is a national phase of International Application No. PCT/IB2006/000989, filed Apr. 24, 2006, which claims the benefit of U.S. Provisional Application No. 60/676,165, filed Apr. 29, 2005. These applications are hereby incorporated by reference in their entirety.

FIELD OF THE INVENTION

The present invention relates to the treatment or prevention of Ovarian Hyperstimulation Syndrome (OHSS) using a dopamine agonist. In some embodiments, the dopamine agonist is quinagolide (Norprolac®), cabergoline (Dostinex®) or bromocriptine (Parlodel®).

BACKGROUND OF THE INVENTION

Infertility afflicts about 5 million American women in the United States (about 10-15%). Many factors may account for infertility including abnormalities of the uterus (such as fibroids); ovarian dysfunction; endometriosis (the presence of uterine tissue in ectopic locations such as the ovaries); scar tissue from previous surgery; thyroid problems or other hormonal imbalances; sexually transmitted diseases or other infections, or unexplained infertility (idiopathic infertility). One primary cause of infertility is chronic anovulation due to hypoestrogenic hypogonadism. This disorder is associated with serum estrogen in the post-menopausal range, normal to low follicle-stimulating hormone (FSH), which causes irregular menses or amenorrhea. These patients usually have normal prolactin levels. A second cause of infertility is attributed to hypergonadotropic hypogonadism. These patients have elevated FSH and postmenopausal estrogen levels. This category includes patients with premature ovarian failure.

Other causes of infertility include hyperprolactinemia, which results in low levels of luteinizing hormone (LH) and FSH, resulting in a failure of the positive feedback response of gonadotropin secretion induced by estrogen; hypothyroidism, which results in hyperprolactinemia; hypothalamic-pituitary dysfunction, caused by low body fat due to excessive weight loss from strenuous exercise, eating disorders, or tumors; luteal phase defects (insufficient progesterone production by the ovary or poor response of the uterus to progesterone); and androgenization, e.g., polycystic ovarian syndrome (PCOS). PCOS is characterized by menstrual disturbances (oligomenorrhea or dysfunctional uterine bleeding), increased male pattern hair growth (hirsutism), acne, alopecia, obesity, and infertility (Blankstein et al., Infertility. 1998; 83: 97-102).

Still additional causes of anovulation include resistant ovary syndrome, autoimmune oophoritis, and premature ovarian failure. Resistant ovary syndrome is characterized by amenorrhea, endogenous hypergonadotropinemia, and resistance to exogenous gonadotropins. Histologically there is an almost complete absence of developing follicles. The exact cause is unknown, and there are several theories including a deficiency of FSH and LH receptors in the ovary, the presence of antibodies to gonadotropin receptors, and a postreceptor defect. Galactosemia not infrequently accompanies resistant ovary syndrome and may be a causative factor. Autoimmune oophoritis is characterized by inflammation of ovaries resulting in their destruction, atrophy, and fibrosis with a loss of fertility and ovary hormonal production. It leads to premature ovarian failure (POF) in 10 percent of cases. Women with POF have premature menopause before 40 years of age.

Lastly, lifestyle habits such as heavy alcohol, and/or caffeine consumption, smoking, or illicit drug use is also associated with decreased fertility.

Infertility is typically treated with ovulation induction agents, commonly referred to as fertility drugs. Exemplary ovulation induction agents include human menopausal gonadotropins (hMG), human chorionic gonadotropin (hCG), clomifene, FSH, luteinizing hormone (LH), gonadotropin-releasing hormone (GnRH) and analogs thereof, and combinations of the foregoing (Derman et al., Drug Safety. 1994; 11: 408-21). These drugs work through different mechanisms, depending on the cause or suspected cause of the infertility. For example, bromocriptine, a dopamine agonist, decrease prolactin secretion in women with hyperprolactinemia, while other agents such as clomifene increase FSH production.

In addition, in vitro fertilization (IVF) is routinely used for all kinds of infertility. IVF involves a process where mature eggs are removed from the ovaries, fertilized with sperm in a laboratory dish, and then the resulting embryos are implanted into the uterus within several days. Prior to egg removal, ovaries are stimulated using fertility drugs such as Pergonal® (hMG) or Metrodin® (a combination of FSH and LH). Several variations of IVF include gamete intrafallopian transfer (GIFT), zygote intrafallopian transfer (ZIFT), Intracytoplasmic sperm injection (ICSI), and intrauterine insemination. In the latter, a purified fraction of highly motile sperm is placed either in the cervix or high in the uterine cavity following ovarian hyperstimulation (also known as "controlled ovarian stimulation" or "ovulation induction") with fertility drugs. Luteal phase defects are more likely to occur with the higher estrogen levels produced during ovulation induction, either alone or with IVF techniques.

Ovarian Hyperstimulation Syndrome

Ovarian Hyperstimualtion Syndrome (OHSS) is a complication of ovarian induction therapy that involves the use of gonadotropin hormones, such as hCG, during fertility treatments or prior to IVF and related procedures. Three grades of OHSS can be distinguished by clinical and sonographic criteria. Mild OHSS is associated with mild abdominal discomfort, including diarrhea, and the ovaries are usually less than 5 cm in diameter on sonographic examination. With moderate OHSS, the ovaries measure between 5 and 10 cm, and in the severe form, the ovaries are greater than 10 cm in diameter. Severe OHSS is characterized by the presence of free intraperitoneal fluid (ascites) due to increased vascular permeability. Pleural effusions, hypotension, and oliguria have also been described. The patient also may have fluid and electrolyte disturbances and is at increased risk for torsion of the enlarged ovaries. Severe OHSS occurs in fewer than 2% of patients.

Hypotension results from extravasation of protein-rich fluid and contraction of the vascular volume, oliguria/anuria from reduced renal perfusion due to decreased vascular volume and/or tense ascites, and pulmonary indications from an elevated diaphragm and/or hydrothorax. Risk of thromboembolism is increased as a result of hemoconcentration, diminished peripheral blood flow, and inactivity due to abdominal distension and pain. Life-threatening complications of OHSS include renal failure, adult respiratory distress syndrome (ARDS), hemorrhage from ovarian rupture, and thromboembolism.

Sonographic and laboratory findings aid in predicting which patients are more likely to develop. Estradiol levels are the most accurate indicator. A value of 4000-6000 pg/mL or greater at the time of hCG administration correlates with a higher risk of developing the syndrome. In addition the development of more than eight follicles in an ovary also correlates with an increased risk for OHSS. Other risk factors for OHSS include The following factors increase the risk independently for developing ovarian hyperstimulation syndrome (OHSS): young age; low body weight; polycystic ovary syndrome (PCOS); high doses of exogenous gonadotropins; high absolute or rapidly rising serum estradiol levels; and previous episodes of OHSS.

Treatment and Prevention. Treatment of mild OHSS typically is the use of an oral analgesic and avoidance of intercourse. For moderate OHSS, treatment consists of more potent analgesics, antiemetics, and frequent monitoring such as by regular sonograms, daily weight monitoring, and frequent serial laboratory determinations of hematocrit, electrolytes, and serum creatinine. In addition, fluid intake and strenuous exercise should be limited. Hospitalization is commonly required for monitoring and treatment of patients having severe OHSS.

For those deemed to be at a high risk for OHSS, lowering the hCG doses by about half is warranted for infertility treatment. In addition, subsequent supplementation with progesterone as opposed to addition of hCG may further reduce the risk of OHSS. Administration of intravenous albumin (25%) is also used when estradiol levels are elevated, or there is a history of prior OHSS, although studies of its efficacy have been mixed, and albumin treatment risks exacerbation of ascites, allergic reactions, and virus/prion transmission.

Although caused primarily by ovulation induction during fertility treatment, OHSS also has been reported in patients having mutations in the follicle-stimulating hormone (FSH) gene Smits et al., New Engl. J. Med. 2003. Volume 349:760-766).

In summary, there remains a need in the art for effective therapies to prevent and treat OHSS.

SUMMARY OF THE INVENTION

The present invention provides a method for preventing ovarian hyperstimulation syndrome comprising administering an effective amount of a dopamine agonist in a pharmaceutically acceptable carrier to a subject who is being treated for infertility with a gonadotropin hormone.

In another embodiment, the infertility treatment is part of a procedure such as in vitro fertilization (IVF), intracytoplasmic sperm injection (ICSI), gamete intrafallopian transfer (GIFT), zygote intrafallopian transfer (ZIFT), and intrauterine insemination during controlled ovarian stimulation or ovulation induction.

Exemplary dopamine agonists contemplated for prevention according to the present invention include quinagolide (Norprolac®), pergolide (Permax®), cabergoline (Dostinex®), pramipexole (Mirapex®), ropinirole (Requip®), talipexole, and bromocriptine (Parlodel®).

In a preferred embodiment, the dopamine agonist is quinagolide (Norprolac®), cabergoline (Dostinex®), or bromocriptine (Parlodel®), more preferably quinagolide (Norprolac®).

In another embodiment, where the disorder is androgenization, the dopamine agonist is not cabergoline (Dostinex®).

In one embodiment, the dose of quinagolide (Norprolac®) used to prevent OHSS is between about 0.025 to 0.6 mg/day, preferably between 0.05 to 0.3 mg/day.

In another embodiment, the dose of cabergoline (Dostinex®) used to prevent OHSS is between about 0.05 to 1.0 mg/day, preferably about 0.5 mg/day.

In yet a third embodiment, the dose of bromocriptine (Parlodel®) used to prevent OHSS is between about 5.0 mg/day to about 25 mg/day.

In one embodiment, the dopamine agonist is administered during controlled ovarian stimulation (with gonadotropins or other agents), and prior to triggering final maturation/ovulation with a gonadotropin hormone.

In another embodiment, the dopamine agonist is administered prior to triggering final ovulation by administering human chorionic gonadotropin.

In another embodiment, the dopamine agonist is administered beginning on the day of administration of human chorionic gonadotropin.

In an alternative embodiment, the dopamine agonist is administered prior to administering human chorionic gonadotropin.

In a further embodiment, the dopamine agonist is administered for between about 5 to about 48 days, preferably between about 7 to about 28 days.

In a further embodiment, the dopamine agonist is administered for between about 5 to about 48 days after administration of gonadotropin for ovarian stimulation, preferably between about 7 to about 28 days after administration of gonadotropin for ovarian stimulation.

In an alternative embodiment, the dopamine agonist is administered for a duration of between about 5 to about 48 days after commencing administration of gonadotropin for ovarian stimulation, preferably between about 7 to about 28 days after commencing administration of gonadotropin for ovarian stimulation.

In an alternative embodiment the dopamine agonist is administered beginning on the day of administration of the gonadotropin hormone and is administered for at least about 6 to 8 days.

In an alternative embodiment the dopamine agonist is administered beginning on the day of administration of the gonadotropin hormone and is administered for between about 6 to 8 days.

In another embodiment, the dopamine agonist cabergoline is administered for from about 6 to 8 days after administration of human gonadotropin hormone.

The present invention also provides a method for treating ovarian hyperstimulation syndrome comprising administering to a subject in need of such treatment an effective amount for treating ovarian hyperstimulation syndrome of a dopamine agonist in a pharmaceutically acceptable carrier.

In one embodiment the ovarian hyperstimulation syndrome is associated with administration of gonadotropin hormone.

In another embodiment, the ovarian hyperstimulation syndrome is idiopathic.

In another embodiment the ovarian hyperstimulation syndrome is associated with pregnancy.

In another embodiment, the ovarian hyperstimulation syndrome is moderate to severe, and the subject may be hospitalized.

Dopamine agonists contemplated for treatment include quinagolide (Norprolac®), pergolide (Permax®), cabergoline (Dostinex®), pramipexole (Mirapex®), ropinirole (Requip®), talipexole, and bromocriptine (Parlodel®).

In a preferred embodiment, the dopamine agonist is quinagolide (Norprolac®), cabergoline (Dostinex®), or bromocriptine (Parlodel®), more preferably quinagolide (Norprolac®).

In another embodiment, the dopamine agonist contemplated for treatment of OHSS excludes bromocriptine (Parlodel®), when used as monotherapy.

According to one embodiment, the dose of quinagolide (Norprolac®) for the treatment of OHSS is at a dose of between about 0.025 mg/day to about 0.6 mg/day, preferably between about 0.05 to about 0.3 mg/day.

In another embodiment, the dose of cabergoline (Dostinex®) used to treat OHSS is between about 0.07 to 1.0 mg/day, preferably about 0.5 mg/day.

In another embodiment, the dose of bromocriptine (Parlodel®) is between about 5.0 to 100 mg/day, preferably about 75 mg/day for severe OHSS.

In another embodiment, the dopamine agonist is administered prior to administering human chorionic gonadotropin.

In yet another embodiment for the treatment of OHSS, the dopamine agonist is administered for a duration of from between about 1 day to about 28 days, preferably between about 7 to about 14 days or until symptoms are relieved or eradicated. Initiation of treatment is begun when OHSS symptoms or signs begin to manifest.

DETAILED DESCRIPTION

The present invention is based, in part, on the discovery that vascular endothelial growth factor (VEGF), a pro-angiogenic cytokine, is involved in the pathogenesis of OHSS, and that VEGF activity can be regulated by the neurotransmitter dopamine.

Vascular Endothelial Growth Factor and OHSS

The existence of a vasoactive molecule released in response to hCG is believed to be the main feature associated with the increased vascular permeability that occurs with development of OHSS, and vascular endothelial growth factor (VEGF) is the main candidate as the hCG mediator (Gomez et al., Endocrinology. 2002; 143, 4339-4348). Experiments in animal models have demonstrated that vascular permeability increases from 2 to about 96 hours following hCG administration in rats previously treated with an ovulation-inducing agent (pregnant mare serum gonadotropin; PMSG) (Gomez et al., supra). In addition, an increase in ascites accumulation in the peritoneal cavity in more than 80% of the OHSS group rats was observed at 48 and 96 hours after hCG. The increase in vascular permeability was associated with a concomitant increase in VEGF mRNA expression by the granulose and endothelial cells of the ovary. Ovarian expression of the VEGF type 2 receptor (VEGF-R2) is also increased after 48 hours, and correlated with increased expression of VEGF mRNA expression at the time of maximal vascular permeability. It was also shown that blocking VEGF-R2 with an antibody (SU5416) caused the reversion of vascular permeability to normal levels.

International PCT applications WO2004/041164 and WO2003/3092595, owned by Merck & Co., describe novel tyrosine kinase inhibitors that can be used to inhibit the phosphorylation of receptor tyrosine kinases, including VEGF receptors. These applications also disclose that the novel tyrosine kinase inhibitors can be used alone, or in combination with ovulation stimulators such as bromocriptine and pregnancy hormones, to treat or prevent OHSS.

However, it has been shown from studies in oncolytic models that anti-angiogenic, i.e., anti-VEGF, compounds, including SU5416, cannot be used due to serious toxic effects. Moreover, VEGF expression is important in the growth and development of the endometrium with advancing stages of the menstrual cycle. VEGF expression has been especially correlated with implantation of the embryo (Welter et al., Exp Clin Endocrinol Diabetes. 2003; 111(1): 33-40). The endometrium develops new capillaries from existing microvessels prior to implantation, and improper vascularization of the endometrium may cause implantation failure and infertility. Accordingly, using VEGF or VEGF-R2 inhibitors to treat or prevent OHSS during fertility treatment would also have the contrary indication of preventing pregnancy.

Dopamine and VEGF Receptors

Recently it has been shown that pharmacological doses of dopamine, acting through the D2 dopamine receptors, can inhibit VEGF-mediated microvascular permeability, proliferation, and migration of endothelial cells in vitro by inducing endocytosis of VEGF-R2 (Basu et al., Nat Med. 2001 May; 7(5):569-74). This was also demonstrated in vivo in dopamine-depleted and D2 receptor knock-out mouse models (Sarkar et al., Am J Physiol Heart Circ Physiol. 2004; 287: H1554-60). In these mouse models, VEGF-induced phosphorylation of VEGF-R2, focal adhesion kinase, and Mitogen-Activated Protein Kinase (MAPK) in the endothelial cells was significantly increased compared with controls. This suggests that endogenous dopamine regulates the signaling cascades required for the in vivo endothelial functions of VEGF.

Dopamine and Hyperprolactinemia

In addition to the foregoing effects on VEGF-R2, dopamine also controls secretion of prolactin. Prolactin is a hormone secreted by the pituitary gland, whose secretion is under tonic inhibitory control by dopamine, which acts via D2-type receptors located on lactotrophs in the pituitary. The primary function of prolactin is to stimulate breast epithelial cell proliferation and induce milk production. Excess production of prolactin, termed hyperprolactinemia, is pathologic, and is associated with decreased fertility, infertility, menstrual irregularities, and loss of sexual function and breast-milk production.

Hyperprolactinemia can be idiopathic, but also has been associated with disorders such as polycystic ovarian syndrome (PCOS) and pituitary adenomas. In one study in women with PCOS and hyperprolactinemia, administration of the dopamine agonist cabergoline, to reduce prolactin, was also shown to reduce the risk of OHSS during ovarian induction with a gonadotropic releasing hormone (GnRH) agonist, follicle stimulating hormone (FSH), and hCG (Papaleo et al., Human Reproduction. 2001; 16: 2263-2266). In two other cases, patients with pituitary adenomas presented with OHSS (Murata et al., J. Clin. Endocrin. And Metabol. 2003; 88: 1988-93; Shimon et al., J. Clin. Endocrin. And Metabol. 2001; 86: 3635-40). In the former case, the patient had enlarged, multicystic ovaries and elevated serum estradiol levels. Daily administration of the dopamine agonist bromocriptine at 5 mg/day normalized ovarian size and reduced estradiol levels to within the normal range. Shortly thereafter the patient underwent surgery to remove the adenoma.

In the second case, the pituitary adenoma was associated with enlarged ovaries, elevated follicle stimulating hormone and prolactin but not elevated estradiol. Treatment with the dopamine agonist cabergoline, 0.5 mg twice per week for three weeks, normalized prolactin levels. Shortly thereafter this patient also underwent surgery to remove the adenoma.

Lastly, dopamine also has been shown to cause renal vasodilatation and diuresis. In one study, docarpamine, an oral dopamine prodrug, was administered to 27 patients with treatment-resistant OHSS (Tsunoda et al., Gynecol Endocrinol. 2003; 17: 281-6). Diuresis was increased in some women, and ascites was decreased.

Dopamine Agonists in the Prevention and Treatment of OHSS

The present invention provides a method for treating or preventing OHSS in women undergoing fertility treatment with gonadotropin hormones, by administration of an effective amount of a dopamine agonist. Dopamine agonists can be safely administered in the luteal phase and in early pregnancy without adverse effects. It is expected that the down-regulation of VEGF-R2, via receptor endocytosis, will reduce the pathologic increased vascular permeability that is associated with OHSS.

Dopamine agonists are primarily used for the treatment of Parkinson's disease due to their neuroprotective effects on dopaminergic neurons. Exemplary dopamine agonists that are contemplated for use according to the present invention include but are not limited to cabergoline, bromocriptine, pergolide, talipexole, ropinirole and pramipexole. Cabergoline (Dostinex®) is a long-acting ergot derivative agonist with a high affinity for D2 receptors. Bromocriptine (Parlodel®) is an ergot alkaloid dopamine receptor agonist. It is a strong D2 receptor agonist and a weak DI receptor antagonist. It stimulates both pre- and post-synaptic receptors. Pergolide (Permax®) is a semisynthetic, clavine ergot derivative dopamine agonist. In contrast to bromocriptine, it is a strong D2 receptor agonist and a weak D1 receptor agonist. Ropinirole (Requip®) is a potent, non-ergoline dopamine agonist. Pramipexole (Mirapex®) is a synthetic amino-benzothiazol derivative and a non-ergot D2/D3 agonist.

Quinagolide (1-propylbenzo[g]quinolin-3-yl)-Norprolac®; formerly CV 205-502) is another, non-ergot, non-ergoline, benzoquinoline dopaminergic agonist that blocks prolactin release. It is described in European patent application EP 0077754 and U.S. Pat. No. 4,565,818 to Nordmann et al. It is presently indicated for the treatment of hyperprolactinemia, especially those associated with pituitary tumors. The maintenance dose varies from patient to patient. Quinagolide is taken once daily in the evening, usually in a dose of between 50-150 micrograms (0.05-0.15 milligrams), and, rarely, up to 300 micrograms.

DEFINITIONS

A "dopamine agonist" refers to any compound which competes with dopamine for binding to the dopamine D2 receptor. Exemplary dopamine agonists include, but are not limited to, those disclosed above, i.e., cabergoline, bromocriptine, pergolide, talipexole, ropinirole and pramipexole. In one embodiment, the dopamine agonist induces receptor endocytosis of VEGF-R2. In a preferred embodiment, the dopamine agonist is quinagolide.

The term "dopamine agonist" also includes various salts and isomers (including stereoisomers and enantiomers) of the dopamine agonists. The term "salts" can include acid addition salts or addition salts of free bases. Examples of acids which may be employed to form pharmaceutically acceptable acid addition salts include inorganic acids such as hydrochloric, sulfuric, or phosphoric acid, and organic acids such as acetic, maleic, succinic, or citric acid, etc. All of these salts (or other similar salts) may be prepared by conventional means. The nature of the salt is not critical, provided that it is non-toxic and does not substantially interfere with the desired pharmacological activity.

"Infertility" refers to the inability of a woman to conceive following at least one year of unprotected intercourse. Infertility includes but is not limited to chronic anovulation caused by any of the following: hypoestrogenic hypogonadism, hypergonadotropic hypogonadism, low body fat, increased stress or anxiety, hypothalamic dysfunction, hypothyroidism, hyperprolactinemia, androgenization (polycystic ovarian syndrome), luteal phase defects, tumors of the pituitary or adrenal gland, primary ovarian failure, resistant ovary syndrome, autoimmune oophoritis, and idiopathic infertility. These disorders are described in more detail above. Other causes of infertility include excessive alcohol or caffeine consumptions, smoking, or illicit drug use.

"Treatment for infertility" includes but is not limited to administration of fertility drugs for ovarian stimulation, or administration of fertility drugs prior to or during in vitro fertilization (IVF), gamete intrafallopian transfer (GIFT), zygote intrafallopian transfer (ZIFT), and intrauterine insemination.

"Fertility drugs" include but are not limited to clomifene (Clomid®), which stimulates FSH and LH secretion, progesterone (Crinone®, Prometrium®), GnRH Factrel®, Lutrepulse®), GnRH agonists (Lupron®, Synarel®, Zoladex®), and leuprolide Acetate (Lupron®) Other fertility drugs include recombinant or purified hMG (a combination of LH and FSH; Pergonal®, Humegon®, Repronex®), hCG (Profasi®, Pregnyl®, Novarel®), FSH (urofollitropin; Fertinex®, Follistim®, Gonal-F®, Metrodin®), and LH. hMG, hCG, LH, and FSH are referred to as the "gonadotropin hormones."

The phrase "pharmaceutically acceptable", as used in connection with compositions of dopamine agonists, refers to molecular entities and other ingredients of such compositions that are physiologically tolerable and do not typically produce untoward reactions (toxicity or side effects) when administered to a mammal (e.g., human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" applied to pharmaceutical compositions of the invention refers to a diluent, excipient, or vehicle with which an active compound (e.g., an 1-aminocyclohexane derivative) is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by E. W. Martin, 18th Edition.

The term "patient" or "subject in need thereof" as used herein refers to a mammal. In particular, the term refers to humans at risk for developing, or diagnosed with OHSS. The diagnosis of OHSS is well within the purview of the skilled physician using standard criteria, including but not limited to increased vascular permeability, increased ovarian size, the presence of ascites, and increased estradiol following hCG administration.

The term "treat" is used herein to mean to relieve or alleviate at least one symptom of a disease in a subject. For example, in relation to OHSS, the term "treat" may mean to improve or relieve or reverse or decrease at least one of the following: increased ovarian size, intraperitoneal ascites, pleural effusions, hypotension oliguria, fluid and electrolyte disturbances, diminished peripheral blood flow, and inactivity due to abdominal distension and pain.

Within the meaning of the present invention, the term "treat" also denotes to delay of the progression of disease in the patients presenting with the aforementioned symptoms or other risk factors associated with OHSS.

The terms "prevent or prevention" means prophylactic use of a dopamine agonist to avert events or symptoms associated with OHSS. In a specific embodiment, the term means to avert the increase in vascular permeability following administration of a gonadotropin hormone.

The term "therapeutically effective amount" is used herein to mean an amount or dose of the dopamine agonist to ameliorate, delay, or prevent a symptom or event associated with OHSS in a subject. Alternatively, a therapeutically effective amount is that which is sufficient to cause an improvement in a clinically significant condition or parameter (according to the attending physician employing one or more of the foregoing sets of criteria) associated with OHSS in an individual in need thereof.

A "responder" is a subject in whom OHSS is prevented, delayed, ameliorated, or otherwise improved following treatment with a dopamine agonist according to the method of the present invention. For example, a responder would be a subject with OHSS whose vascular permeability decreases upon administration of an effective amount of a dopamine agonist.

The terms "about" and "approximately" shall generally mean an acceptable degree of error or variation for the quantity measured given the nature or precision of the measurements. Typically, degrees of error or variation are within 20 percent (%), preferably within 10%, and more preferably within 5% of a given value or range of values. Numerical quantities given herein are approximate unless stated otherwise, meaning that the term "about" or "approximately" can be inferred when not expressly stated.

Formulation, Dosage, and Administration

The below-mentioned dopamine agonists are commercially available for oral administration as follows:

quinagolide hydrochloride (Norprolac®)—administration of tablets for hyperprolactinemia is at an initial dose of 0.025 mg daily for 3 days increasing thereafter at 3-day intervals in steps of 0.025 mg until the optimal response is achieved, which is usually within the range of 0.75 to 1.50 mg daily. If doses greater than 3.0 mg daily are required, increases may be made in steps of 0.75 to 1.50 mg daily at intervals of not less than 4 weeks. For treatment and prevention of OHSS, the dosage contemplated is about 0.025-0.6 mg/day, preferably about 0.05 to about 0.3 mg/day.

bromocriptine mesylate (Parlodel®)— administration of tablets or capsules typically is at an initial does of about 2.5 mg/day for 1 week, increased to about 2.5 mg twice a day for another week to 8 weeks. However the effective dosage range of 1.25-20.0 mg/day has been determined. For treatment and prevention of OHSS, it is contemplated that about 5.0 mg to 25 mg/day of bromocriptine will be effective for prevention, preferably about 25 mg/day, and about 75-100 mg/day will be effective for treatment of severe OHSS, preferably about 75 mg/day. Doses may be adjusted downwards for mild and moderate OHSS, e.g., from about 25 mg/day to 75 mg/day.

pergolide mesylate (Permax®)— administration of tablets is a single daily dosage of 0.05 mg for the first two days, gradually increased by 0.1 or 0.15 mg/day every third day over the next 12 days of therapy. The dosage may then be increased by 0.25 mg/day every third day until an optimal therapeutic dosage is achieved, i.e., about 3 mg/day; the dose for the treatment or prevention of OHSS is expected to be lower and can be readily determined by the skilled artisan;

cabergoline (Dostinex®)—administration of tablets for initiation of therapy for hyperprolatinemia is 0.25 mg twice a week. Dosage may be increased by 0.25 mg twice weekly up to a dosage of 1.0 mg twice a week according to the patient's serum prolactin level. For the prevention or treatment of OHSS, the effective dosage contemplated is about 0.05 to 1.0 mg/day (i.e., the total dose given over about 8 days is similar to the dose necessary per day to inhibit lactation, which is about 0.5 mg per day);

talipexole hydrochloride—administration of tablets for Parkinsonism is at doses of about 1.2 to 3.6 mg daily, in divided doses by mouth; the dose for the treatment or prevention of OHSS is expected to be lower and can be readily determined by the skilled artisan;

pramipexole dihydrochloride monohydrate (Mirapex®)— administration of tablets for Parkinsonism is an initial dose of pramipexole hydrochloride of 0.125 mg given three times daily, increased to 0.250 mg three times daily in the second week, and then to 0.5 mg three times daily in the third week according to response. the dose for the treatment or prevention of OHSS is expected to be lower and can be readily determined by the skilled artisan;

ropinirole hydrochloride (Requip®)— administration of tablets for Parkinsonism is at an initial daily dose of about 0.75 mg per day, increased at weekly intervals in steps of 0.75 mg until the optimal response is achieved, which is usually within the range of 3 to 9 mg daily; The daily dosage should not exceed 24 mg. the dose for the treatment or prevention of OHSS is expected to be lower and can be readily determined by the skilled artisan.

However, for any dopamine agonist used in the method of the invention, the therapeutically effective dose can be estimated initially from animal models to achieve a circulating plasma concentration range that includes the $IC_{50}$ (e.g., the concentration of the test compound which achieves a half-maximal secretion of the appropriate hormone). Dose-response curves derived from animal systems are then used to determine testing doses for the initial clinical studies in humans. In safety determinations for each composition, the dose and frequency of administration should meet or exceed those anticipated for use in the clinical trial.

Other factors to consider are the dosage procedure, the conditions of a patient or a subject animal such as age, body weight, sensitivity, dosage period, drugs used in combination, seriousness of the disease. The appropriate dose and dosage times under certain conditions can be determined by the test based on the above-described indices but may be refined and ultimately decided according to the judgment of the practitioner and each patient's circumstances (age, general condition, severity of symptoms, etc.) according to standard clinical techniques.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$. Compositions that exhibit large therapeutic indices are preferred.

According to the invention, the pharmaceutical composition of the invention, e.g., the dopamine agonist, can be introduced parenterally, transmucosally, orally (per os), nasally, or rectally, or transdermally. Parental routes include intravenous, intra arteriole, intramuscular, intradermal, subcutaneous, intraperitoneal, intraventricular, and intracranial administration.

According to the present invention, the dosage form of the dopamine agonist may be a solid, semisolid or liquid formulation for oral administration. Formulation of the dopamine agonist in semi-solid or liquid form is within the skill of the art. Usually the active substance, e.g., the dopamine agonist, will constitute between 0.1 and 99% by weight of the formulation, more specifically between 0.5 and 20% by weight for formulations intended for injection and between 0.2 and 50% by weight for formulations suitable for oral administration.

Oral dosage formulations are well known in the art and include tablets and capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art.

Liquid preparations for oral administration of the dopamine agonist may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

The pharmaceutical dopamine agonist formulations suitable for injectable use include sterile aqueous solutions (where water soluble), emulsions in oils (where not water soluble), or dispersions. In all cases, the form must be sterile and must be fluid to the extent that easy syringability exists. The dosage form must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, sorbic acid, and the like. In many cases, it will be preferable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the dopamine agonist in the required amount in the appropriate solvent with various of the other ingredients, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

In addition to the formulations described above, the dopamine agonist may also be formulated as a depot preparation. Such long acting formulations may be administered by implantation (for example subcutaneously or intramuscularly) or by intramuscular injection.

For prevention of OHSS, administration of the dopamine agonist can be according to two alternative regimens. In one embodiment, the dopamine agonist is administered during controlled ovarian stimulation (with gonadotropins or other agents), and prior to triggering final maturation/ovulation with a gonadotropin hormone. In this embodiment, the dopamine agonist is administered for a duration of about 5 to about 48 days, preferably about 7 to 28 days.

In an alternative embodiment the dopamine agonist is administered beginning on the day of administration of the gonadotropin hormone and is administered for about 6 to 8 days.

Combination Therapy

The present invention also contemplates combinations of dopamine agonists for the treatment or prevention of OHSS. In one embodiment, the combination permits subthreshold or suboptimal doses of one or both of the dopamine agonists administered in combination.

The term "subthreshold" referring to the amount of an active ingredient, such as a dopamine agonist, means an amount inadequate to produce a response, i.e., an amount below the minimum effective amount. The term "suboptimal" in the same context means an amount of an active ingredient, such as a dopamine agonist, that produces a response but not to its full extent, which would be achieved with a higher amount.

Said combination of dopamine agonists can be either formulated as a single composition or as two separate compositions, which can be administered conjointly.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

Genes Up- and Down-Regulated in OHSS Associated with Vascular Permeability and Use of Bromocriptine to Reduce Vascular Permeability Associated with OHSS)

Using microarray technology (Affymetrix, Inc. Santa Clara, Calif.), the pattern of gene up- and down-regulation was examined in control, hyperstimulated, and OHSS rat ovaries.

Methods

Drug Treatment. Immature female Wistar rats were employed. In the OHSS group (n=8), Pregnant Mare's Serum Gonadotropin (PMSG) was administered at 10 IU/day for 4 days, followed by hCG (30 IU) on the fifth day. In the mild (i.e., ovarian stimulation) group (n=8), 10 IU of PMSG was administered followed 2 days later by administration of 10 IU of hCG. In the control group, 1 IU of PMSG was administered followed by 1 IU of hCG 48 hrs later.

Vascular Permeability Measurement. Vascular permeability was measured 48 hours following hCG administration. 0.2 ml of 5 mM Evans Blue stain was injected via the femoral vein. After 30 minutes, the peritoneal cavity was irrigated with saline. Light absorption was measured in the recovered fluid at 595 nm and the vascular permeability was expressed as µg Evans blue/100 g body weight.

Measurement of Gene Expression. mRNA from ovaries was extracted for use in the gene expression assay using a microarray containing about 14,000 genes. Genes which were up- or down-regulated at least 3 fold were considered to be significantly affected. Confirmation of gene expression was achieved by quantitative fluorescent PCR in an ABI-PRISM 7700 thermocycler to amplify 3 up-regulated and 3 down-regulated genes. Additional confirmation was performed using immunostaining according to ordinary protocols, and using cluster analysis. The latter was performed by reverse transcribing RNA and transfer to nylon filters under radioactive conditions. Clusters of 5×5 spot signals were analyzed using the AIDA software, and its expression was paired to the other groups following background signal subtraction.

In a second series of experiments, varying doses of bromocriptine were administered in a group of rats induced to develop OHSS with 40 IU of PMSG followed by 30 IU of hCG. 1.6, 4.0, 10.0 and 25.0 mg/kg of bromocriptine were intraperitoneally administered on the day of hCG administration and 24 hours later. VP was measured 48 hours following hCG administration.

Results

Gene Expression. Gene expression in the three groups in the first experiments showed 80 up-regulated and 7 down-regulated genes in OHSS as compared with the mild and control groups. The up-regulated genes were grouped into five families as follows: cholesterol synthesis, VEGF signal transduction, prostaglandin synthesis, oxidative stress, and prolactin synthesis. Tyrosine hydroxylase (TH), the rate-limiting enzyme required for the production of dopamine, was the primary down-regulated gene of interest in the OHSS ovaries. Specifically, TH catalyses the conversion of L-tyrosine to L-dopamine.

Bromocriptine Treatment. The OHSS animals from the initial experiment exhibited increased vascular permeability (30.7±5.8 µg Evans Blue/100 g body weight). This was reduced upon treatment of 1.6 mg bromocriptine (15.3±3.3; p=0.04); 4 mg bromocriptine (14.2±2.2; p=0.04); 10 mg bromocriptine (10.1±2.6; p=0.009; and 25 mg bromocriptine (8.0±1.9; p=0.001).

These results, notably the up- and down-regulation of genes involved in VEGF, prolactin and dopamine expression, encourage the use of bromocriptine to prevent pathologic increases in vascular permeability and use for the prevention/treatment of OHSS. It is expected that other dopamine agonists will have similar effects on VEGF and therefore will also be useful for the prevention and treatment of OHSS.

Example 2

Prevention or Treatment of OHSS Using Quinagolide (Norprolac®)

For prevention of OHSS in patients undergoing fertility treatment or IVF involving the administration of gonadotropin hormones, it is expected that administration of the dopamine agonist quinagolide will prevent an increase in vascular permeability. Without being limited to a particular mechanism, it is expected that this will occur as a result of quinagolide binding to dopamine D2 receptors, resulting in internalization of VEGF-R2, thereby preventing binding of VEGF-A to VEGF-R2 and phosphorylation of VEGF-R2.

Dosage and Administration. Quinagolide can be given orally over the course of about 8 days, starting the day of hCG administration for fertility or IVF treatment. The dosage should be about 0.025-0.6 mg/day, preferably about 0.05 to about 0.3 mg/day (i.e., the dose similar to that required to inhibit lactation).

Alternatively, for prevention, cabergoline is administered during controlled ovarian stimulation (with gonadotropins or other ovarian stimulating agents) prior to triggering final maturation/ovulation with e.g., hCG. Preferably, administration is initiated during the last week of stimulation. Administration is continued for about one to three weeks after hCG stimulation.

Treatment of OHSS. For treatment of mild to severe OHSS, administration of quinagolide is initiated once a patient has been diagnosed with mild to severe OHSS, and continued for a duration of about 1 to 28 days, or until symptoms abate. Again, quinagolide will be employed to decrease the increased vascular permeability and thus, will be administered until the symptoms are reversed or relieved.

Dosage and Administration. For treatment of OHSS, quinagolide is administered at a dose of about 0.025 mg/day to about 0.6 mg/day, preferably about 0.05 mg/day to about 0.3 mg/day. Duration of treatment is about 1 to 28 days, preferably 7 to 14 days, or until symptoms abate. Treatment is typically initiated when signs and symptoms of OHSS first appear.

Example 3

Prevention or Treatment of OHSS Using Cabergoline (Dostinex)®

Prevention of OHSS. For prevention of OHSS in patients undergoing fertility treatment or IVF involving the administration of gonandotrophic hormones, it is expected that administration of the dopamine agonist cabergoline will prevent an increase in vascular permeability. Without being limited to a particular mechanism, it is expected that this will occur as a result of cabergoline binding to dopamine D2 receptors, resulting in internalization of VEGF-R2, thereby preventing binding of VEGF-A to VEGF-R2 and phosphorylation of VEGF-R2.

Dosage and Administration. For prevention of OHSS, cabergoline may be given over the course of about 8 days, starting the day of hCG administration for fertility or IVF treatment. The dosage should be about 0.05 to 1.0 mg/day (i.e., the total dose over about 8 days is similar to the dose necessary per day to inhibit lactation, which is about 0.5 mg per day).

Alternatively, for prevention, cabergoline (Dostinex®) is administered during controlled ovarian stimulation (with gonadotropins or other ovarian stimulating agents) prior to triggering final maturation/ovulation with e.g., hCG. Preferably, administration is initiated during the last week of stimulation. Administration is continued for about one to three weeks after hCG stimulation.

Treatment of OHSS. For treatment of mild to severe OHSS, administration of cabergoline is initiated once a patient has been diagnosed with mild or moderate to severe OHSS, and is probably hospitalized. Again, cabergoline will be employed to decrease the increased vascular permeability.

Dosage and Administration. For treatment of OHSS, administration of cabergoline is initiated once a patient has been diagnosed with moderate to severe OHSS. Cabergoline will be administered at a dose of about 0.05 to about 1.0 mg/day until symptoms are reversed or relieved. Duration of treatment will be from about 1 to about 28 days, preferably from about 7 to about 14 days, or until symptoms abate. Treatment is initiated when signs and symptoms of OHSS first appear.

Examples 4 and 5

Dose/Response Measurement of the Effects of Quinagolide (Norprolac®) on Vascular Permeability in OHSS Rats General Procedures Inducing OHSS manifestations. A total of 96 female immature Wistar rats (Harlan Iberica, Sant Feliu de Codina, Barcelona, SPAIN), weighing from 42-48 grams at the beginning of these experiments (day 22), were used to carry out the studies disclosed in Examples 4 and 5. They were injected subcutaneously (s.c) with 10 IU of Pregnant Mare's Serum Gonadotropin (PMSG) (Sigma) for 4 consecutive days (days 22-25), followed by administered intraperitoneally (i.p.) with 30 IU of hCG on the fifth day (day 26) in order to induce OHSS clinical manifestations.

Measuring vascular permeability (VP). VP was used as an index to estimate and compare the degree of development of the illness. VP was measured in all animals 48-56 hours after hCG administration, following methodology previously described (Gomez et al., supra). Briefly, 0.2 ml Evans Blue dye, 0.05 M, was injected through the femoral vein. After 30 minutes, the peritoneal cavity was irrigated with 5 ml saline, pH 6, 22° C., and massaged for 30 seconds to recover extravasated dye. The peritoneal fluid was recovered in 13 ml tubes containing 0.1 ml NaOH. The tubes were centrifuged at 900×g for 12 minutes to avoid protein interference. The supernatant was filtered through 0.22 um filters in order to eliminate ascitic protein/fibrin mucus which could interfere in the posterior measurements. Finally the absorbance of the extravasated dye was measured at 595 nm using a spectrophotometer. Average and average deviations in each group (see below) were calculated. VP was expressed as µg extravasated Evans Blue dye/100 g body weight in each animal. These units have been expressed as the "y" axes of the graphs presented in FIGS. 1 and 2.

Example 4

Dose Response Experiments Assaying the Effect of Quinagolide on Vascular Permeability in OHSS Rats A total of 70 rats were used for this study. All 70 rats were administered PMSG/hCG to induce OHSS symptoms, as described above. Quinagolide (batch no. 1010003004; supplied by Ferring Labs) was administered to 56 rats. The 56 rats that received quinagolide were used as a dose response test group. Eight rats did not receive quinagolide, and were used as a vehicle control group. Cabergoline (Dostinex®) was administered to 6 rats as a positive control. The specific details of the dosing regimen for each group is as follows:

Vehicle control group (quinagolide 0 µg/kg) (n=8). Eight rats were implanted with prolactin placebo pellets, 5 days release, between 10:00 to 11:00 on day 26, just following hCG injection (see General Procedures, above). Six hours after pellet implantation, the rats in this group were orally administered vehicle solution (1:6 alcohol in water mixture) (without quinagolide). They received another oral vehicle administration of vehicle solution 24 hours later.

Experimental groups (quinagolide at 0.1, 0.3, 1, 3, 10, 25, 50 µg/kg/day to 7 test groups of rats) (n=8 in each test group). The rats in these groups were implanted with prolactin pellets, 5 days release, between 10:00 to 11:00 on day 26, just following hCG injection (see General Procedures, above). Six hours after pellet implantation (so that prolactin had an appropriate time window to be released), the rats in these seven test groups received an oral administration of quinagolide of 0.008, 0.025, 0.08, 0.25, 0.8, 2, 4 µg, respectively, diluted in 100 µl vehicle solution. In this manner, the desired 0.1, 0.3, 1, 3, 10, 25, 50 µg/kg doses to be assayed were achieved. Twenty four hours later, the rats in this group were administered with another dose of the same amounts of quinagolide.

Positive (cabergoline) control group (n=6). These six rats were implanted with prolactin pellets, 5 days release, between 10:00 to 11:00 .m on day 26, just following hCG injection. Six hours after pellet implantation (so that prolactin had an appropriate time window to be released), the rats in this group were administered with cabergoline 12 µg diluted in 100 µl vehicle (reaching a 150 µg/kg dose). Twenty four hours later, the rats in this group were administered with another dose of the same amount of cabergoline. This dosage of cabergoline (250 µg/kg/day) was chosen based on previous experiments performed by this group (repeated several times), demonstrating a high correlation (p<0.05) between this dosage of cabergoline and a significant decrease in vascular permeability in OHSS rats.

Reconstitution and dilution process to reach appropriate quinagolide doses for oral administration. Appropriate doses were prepared fresh just prior to being administered (on day 26). A single quinagolide vial, containing approximately 2.30-2.30 mg quinagolide, was employed for each single set of animals. For each solution, approximately 2.30-2.30 mg quinagolide was diluted in a vehicle solution (1:6 alcohol: water mixture) to achieve a stock concentration of 100 µg quinagolide per ml solution. A 2 ml aliquot of the quinagolide stock solution was serially diluted in the same vehicle solution, to achieve seven solutions with the following concentrations: 0.08, 0.25, 0.8, 2.5, 8, 20, and 40 µg quinagolide per ml solution, respectively. A 100 µl oral administration of each quinagolide solution was given to the appropriate rat group on the same day hCG was administered (day 26), as described below. The residual stock was stored at 4° C., to be used in the same way 24 hours later, as described below. 100 μl of each serially diluted solution contained 0.008, 0.025, 0.08, 0.25, 0.8, 2, and 4 μg quinagolide, respectively. Thus, given that the rats weighed, on average, 75-80 g on day 26 (when quinagolide was administered), the desired 0.1, 0.3, 1, 3, 10, 25, 50 μg/kg doses were achieved. This vehicle solution (1:6 alcohol:water mixture), without quinagolide, was administered to the positive control group of rats, as described.

Reconstitution and dilution of cabergoline to reach appropriate dose for oral administration. A Half-One (Dostinex®) pill containing 125 μg cabergoline was pulverized mechanically, then diluted in 1000 μl of a vehicle solution (1:6 alcohol:water mixture), to achieve a final concentration of 125 μg cabergoline per ml solution. A 100 μl oral administration of this solution was performed on the day of hCG administration as described below. The residual stock was stored at 4° C., to be used in the same way 24 hours later, as described. 100 μl of this solution contains 12.5 μg cabergoline. Thus, given that the rats weighed, on average, 75-80 g on day 26 (when cabergoline was administered), the desired 150 μg/kg doses were achieved.

Vascular permeability (VP) was measured in all rats between 48 and 56 hours after hCG administration, at 17:00 and 20:00 h, which coincides with the nocturnal peak prolactin release time. Prolactin endogenous release is expected to be totally blocked in rats treated with quinagolide. Therefore, the time at which prolactin measurements are performed is not crucial in quinagolide-treated rats. However, the time at which prolactin measurements are performed in OHSS rats untreated with quinagolide is crucial. Therefore, vascular permeability was measured in all rats at 48 and 56 hours after hCG administration, in order to reduce variability as much as possible. In addition, because it is technically difficult to measure VP in more than 4-6 animals each hour, and these measurements were required to be completed within a 3 hour interval, the tests were staggered over four consecutive days, using sets (designated Sets 1-4 in Table 1, below) of 16-18 rats each day.

Results

VP data for approximately 25% of the rats were lost because of a problem associated with the filters used to avoid protein interference. A contaminant is believed to have been present in one lot of the filters. As a result, the Evans blue dye changed to a pale green or yellow color just after its passage through the filter. The contaminated filters were replaced once the problem was identified. Nevertheless, most of the extravasated peritoneal liquids obtained for Set 3 were lost (as indicated in the raw data set forth in Table 1, below).

TABLE 1

Raw data: effect of quinagolide on vascular permeability in OHSS rats

| Rat number | Quinagolide (μg/kg/day) | Rat body weight (g) | Absorbance at 595 nm | μg Evans Blue (Abs * 4360) | μg EB per 100 g body weight |
|---|---|---|---|---|---|
| Set 1 | | | | | |
| 1 | 0 | 77 | 0.468 | 2040.48 | 26.49974026 |
| 2 | 0.1 | 72 | 0.35 | 1526 | 21.19444444 |
| 3 | 0.3 | 72 | 0.28 | 1220.8 | 16.95555556 |
| 4 | 1 | 62 | 0.396 | 1726.56 | 27.84774194 |
| 5 | 3 | 66 | 0.09 | 392.4 | 5.945454545 |
| 6 | 10 | 74 | 0.418 | 1822.48 | 24.62810811 |
| 7 | 25 | 68 | 0.299 | 1303.64 | 19.17117647 |
| 8 | 50 | 72 | 0.179 | 780.44 | 10.83944444 |
| 9 | Cb: 150 ug/kg | 72 | 0.356 | 1552.16 | 21.55777778 |
| 10 | 0 | 75 | 0.405 | 1765.8 | 23.544 |
| 11 | 3 | 74 | peritoneum broken, saline not retained | | |
| 12 | 0.3 | 65 | 0.547 | 2384.92 | 36.69107692 |
| 13 | 1 | 66 | 0.341 | 1486.76 | 22.52666667 |
| 14 | 3 | 64 | 0.394 | 1717.84 | 26.84125 |
| 15 | 10 | 74 | 0.145 | 632.2 | 8.543243243 |
| 16 | 25 | 70.5 | 0.311 | 1355.96 | 19.23347518 |
| 17 | 50 | 73.5 | 0.048 | 209.28 | 2.847346939 |
| Set 2 | | | | | |
| 18 | Cb: 150 ug/kg | 70 | 0.034 | 148.24 | 2.117714286 |
| 19 | 0 | 72.5 | 0.363 | 1582.68 | 21.83006897 |
| 20 | 0.1 | 72.5 | 0.081 | 353.16 | 4.871172414 |
| 21 | 0.3 | 70 | 0.768 | 3348.48 | 47.83542857 |
| 22 | 1 | 76 | 0.389 | 1696.04 | 22.31631579 |
| 23 | 3 | 79.5 | 0.181 | 789.16 | 9.926540881 |
| 24 | 10 | 66 | 0.188 | 819.68 | 12.41939394 |
| 25 | 25 | 69 | 0.042 | 183.12 | 2.653913043 |
| 26 | 50 | 72 | 0.151 | 658.36 | 9.143888889 |
| 27 | Cb: 150 ug/kg | Rat died | | | |
| 28 | 0 | 72.5 | 0.303 | 1321.08 | 18.2217931 |
| 29 | 0.1 | 74.5 | 0.646 | 2816.56 | 37.8061745 |
| 30 | 0.3 | 72.5 | 0.342 | 1491.12 | 20.56717241 |
| 31 | 1 | 70 | 0.424 | 1848.64 | 26.40914286 |
| 32 | 3 | 68.5 | 0.584 | 2546.24 | 37.17138686 |
| 33 | 10 | 72.5 | 0.328 | 1430.08 | 19.72524138 |
| 34 | 25 | 72 | 0.669 | 2916.84 | 40.51166667 |
| 35 | 50 | 68 | 0.358 | 1560.88 | 22.95411765 |
| | | | | 4360 | #DIV/0! |

TABLE 1-continued

Raw data: effect of quinagolide on vascular permeability in OHSS rats

| Rat number | Quinagolide (μg/kg/day) | Rat body weight (g) | Absorbance at 595 nm | μg Evans Blue (Abs * 4360) | μg EB per 100 g body weight |
|---|---|---|---|---|---|
| | | | Set 3 | | |
| 1 | 25 | 73 | LOST | | |
| 2 | 10 | 72.5 | LOST | | |
| 3 | 3 | 75 | LOST | | |
| 4 | 1 | 81 | LOST | | |
| 5 | 0.3 | 75 | LOST | | |
| 6 | 0.1 | 80 | LOST | | |
| 7 | 0 | 78 | LOST | | |
| 8 | Cb: 150 ug/kg | 67 | 0.1 | 436 | 6.507462687 |
| 9 | 25 | 80 | LOST | | |
| 10 | 10 | 82 | LOST | | |
| 11 | 3 | 75 | LOST | | |
| 12 | 1 | 81 | LOST | | |
| 13 | 0.3 | 75 | LOST | | |
| 14 | 0.1 | 81 | LOST | | |
| 15 | 0 | 82 | LOST | | |
| 16 | Cb: 150 ug/kg | 70 | 0.1 | 436 | 6.228571429 |
| | | | Set 4 | | |
| 17 | 25 | 74 | LOST | | |
| 18 | 10 | 81 | LOST | | |
| 19 | 3 | 69 | 0.369 | 1608.84 | 23.31652174 |
| 20 | 1 | 78 | 0.256 | 1116.16 | 14.30974359 |
| 21 | 0.3 | 80 | LOST | | 0 |
| 22 | 0.1 | 76 | LOST | | |
| 23 | Control | 73 | 0.494 | 2153.84 | 29.50465753 |
| 24 | Cb: 150 ug/kg | 71 | 0.293 | 1277.48 | 17.99267606 |
| 25 | 25 | 77.5 | 0.08 | 348.8 | 4.500645161 |
| 26 | 10 | 73 | 0.626 | 2729.36 | 37.38849315 |
| 27 | 3 | 81.5 | 0.581 | 2533.16 | 31.08171779 |
| 28 | 1 | 72.5 | 0.205 | 893.8 | 12.32827586 |
| 29 | 0.3 | 75 | 0.444 | 1935.84 | 25.8112 |
| 30 | 0.1 | 70 | 0.338 | 1473.68 | 21.05257143 |
| 31 | Control | 78 | 0.327 | 1425.72 | 18.27846154 |
| 32 | 50 | 74.5 | 0.09 | 392.4 | 5.267114094 |
| 33 | 50 | 75 | 0.215 | 937.4 | 12.49866667 |

Key:
EB = Evans Blue
Cb = cabergoline (used as positive control)

Figure 1:
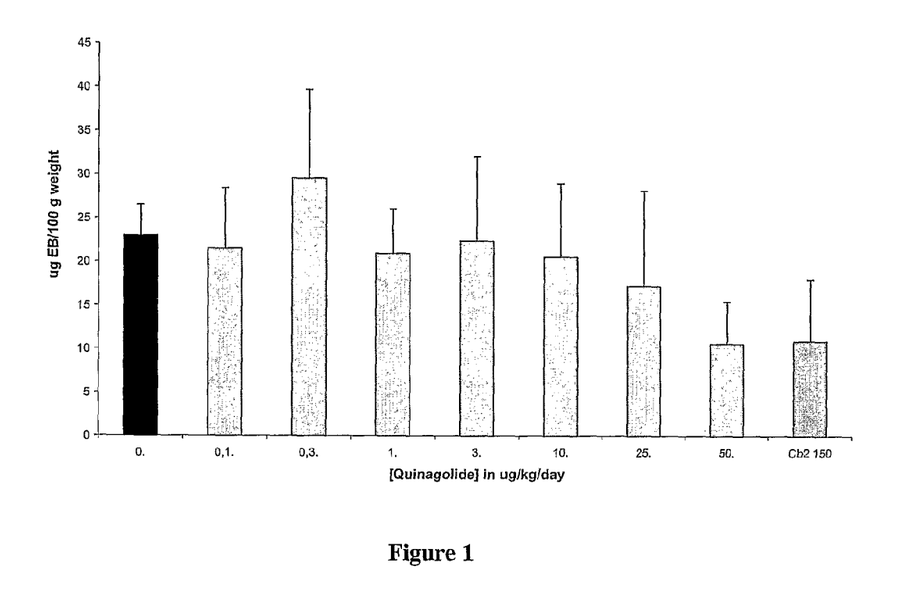
FIG. 1 is a graph depicting the results of a first assay on the effect of quinagolide on VP in OHSS rats. Vascular Permeability is expressed as µg extravasated Evans Blue dye per 100 g body weight in each animal.

Vascular Permeability is expressed as μg extravasated Evans Blue dye per 100 g body weight in each animal. The raw data from Table 1, above, were used to generate the results depicted in graphic form in FIG. 1. The results presented in FIG. 1 represent the average of the results for the vehicle controls (no quinagolide), positive controls (cabergoline), and for each of the administered amounts of quinagolide (0.1, 0.3, 1, 3, 10, 25, and 50 μg/kg body weight), in each rat so tested.

Example 5

Dose Response Experiments Assaying the Effect of Quinagolide on Vascular Permeability in OHSS Rats (Reassessment)

Because some of the Example 4 data was lost (See Table 1), Example 5 was performed to reassess the effect of quinagolide on vascular permeability in OHSS rats.

For Example 5, three quinagolide doses were tested: 5, 50 250 μg/kg/day. The 250 μg/kg/day dose was tested in order to determine if the maximal potential inhibitory effect of quinagolide had been reached in Example 4.

The General Procedures were performed as set forth above.

A total of 26 rats were used for this study. All 26 rats were administered PMSG/hCG to induce OHSS symptoms, as described above. Quinagolide was administered to 18 rats, divided into three groups of six rats per group. The 18 rats that received quinagolide were used as a dose response test group. Eight rats did not receive quinagolide, and were used as a vehicle control group. A positive control group was not employed for this Example. The specific details of the dosing regimen for each group is as follows:

Vehicle control group (quinagolide 0 μg/kg) (n=8). Eight rats were implanted with prolactin placebo pellets, 5 days release, between 10:00 to 11:00 on day 26, just following hCG injection (see General Procedures, above). Six hours after prolactin placebo pellet implantation, the rats in this group were orally administered vehicle solution (1:6 alcohol:water mixture) (without quinagolide). They received another oral administration of vehicle solution 24 hours later.

Experimental groups (quinagolide at 5, 62.5, 250 μg/kg/day to 3 test groups of rats) (n=6 in each test group). These rats were implanted with prolactin pellets, 5 days release, between 10:00 to 11:00 am on day 26, just following hCG injection (see General Procedures, above). Six hours after prolactin pellet implantation (so that prolactin had an appropriate time window to be released), the rats in these three test groups (six rats/group) received an oral administration of quinagolide of 0.4, 5, 0.08, and 20 μg, respectively, diluted in 250 μl vehicle solution. In this manner, the desired 5, 62.5, and 250 μg/kg doses to be assayed were achieved. Twenty four hours later, the rats in this group were administered with another dose of the same amounts of quinagolide.

Reconstitution and dilution process to reach appropriate quinagolide doses for oral administration. A commercial drug, Norprolac®, was used as the source of quinagolide for this Example. Four Norprolac® pills, containing 150 μg quinagolide each (600 μg quinagolide total) were diluted in 6250 μl of distilled water. A volume of 1250 μl of alcohol was added to reach a vehicle solution (1:6 alcohol:water mixture) containing 80 μg quinagolide per ml solution. A 1.5 ml aliquot was serially diluted (1:4, 1:12.5) in the same vehicle solution. A 250 μl oral administration of each quinagolide solution was given to the appropriate rat in each group on the same day hCG was administered (day 26), as described. The residual stock was stored at 4° C., to be used in the same way 24 hours later, as described. 250 μl of each serially diluted solution contained 0.4, 5, and 20 μg quinagolide, respectively. Thus, given that the rats weighed, on average, 75-80 g on day 26 (when quinagolide was administered), the desired 5, 50, and 250 μg/kg doses were achieved. The vehicle solution (1:6 alcohol:water mixture), without quinagolide, was administered to the positive control group of rats, as described.

Results

The raw data obtained for Example 5 is set forth in Table 2, below.

TABLE 2

Raw data: effect of quinagolide on vascular permeability in OHSS rats (reassessed)

| Rat number | Quinagolide (μg/kg/day) | Rat body weight (g) | Absorbance at 595 nm | μg Evans Blue (Abs * 4360) | μg EB per 100 g body weight |
|---|---|---|---|---|---|
| 1 | 66 | 5. | 0.335 | 1460.6 | 22.13030303 |
| 2 | 71.5 | 62. | 0.201 | 876.36 | 12.25678322 |
| 3 | 76 | 250. | 0.03 | 130.8 | 1.721052632 |
| 4 | 76 | 0. | 0.493 | 2149.48 | 28.28263158 |
| 5 | 70 | 5. | 0.622 | 2711.92 | 38.74171429 |
| 6 | 69.5 | 62. | 0.115 | 501.4 | 7.214388489 |
| 7 | 55 | 250. | 0.036 | 156.96 | 2.853818182 |
| 8 | 72 | 0. | 0.394 | 1717.84 | 23.85888889 |
| 9 | 72.5 | 5. | 0.924 | 4028.64 | 55.56744828 |
| 10 | 72.5 | 62. | 0.125 | 545 | 7.517241379 |
| 11 | 68.5 | 250. | 0.1709 | 745.124 | 10.87772263 |
| 12 | 74 | 0. | 0.294 | 1281.84 | 17.32216216 |
| 13 | 74.5 | 5. | 0.491 | 2140.76 | 28.73503356 |
| 14 | 69.5 | 62. | 0.256 | 1116.16 | 16.05985612 |
| 15 | 67.5 | 250. | 0.021 | 91.56 | 1.356444444 |
| 16 | 64 | 0. | 0.617 | 2690.12 | 42.033125 |
| 17 | 72 | 5. | 0.181 | 789.16 | 10.96055556 |
| 18 | 68.5 | 62. | 0.209 | 911.24 | 13.30277372 |
| 19 | 67 | 250. | 0.103 | 449.08 | 6.702686567 |
| 20 | 69 | 0 | blood contamination | 0. | #VALUE! |
| 21 | 66 | 0 | 0.42 | 1831.2 | 27.74545455 |
| 22 | 71.5 | 5. | 0.242 | 1055.12 | 14.75692308 |
| 23 | 71.5 | 0. | 0.473 | 2062.28 | 28.84307692 |
| 24 | 68.5 | 62. | 0.299 | 1303.64 | 19.03124088 |
| 25 | 77 | 0. | 1.03 | 4490.8 | 58.32207792 |
| 26 | 69.5 | 250. | 0.056 | 244.16 | 3.513093525 |

Key:
EB = Evans Blue

Figure 2:
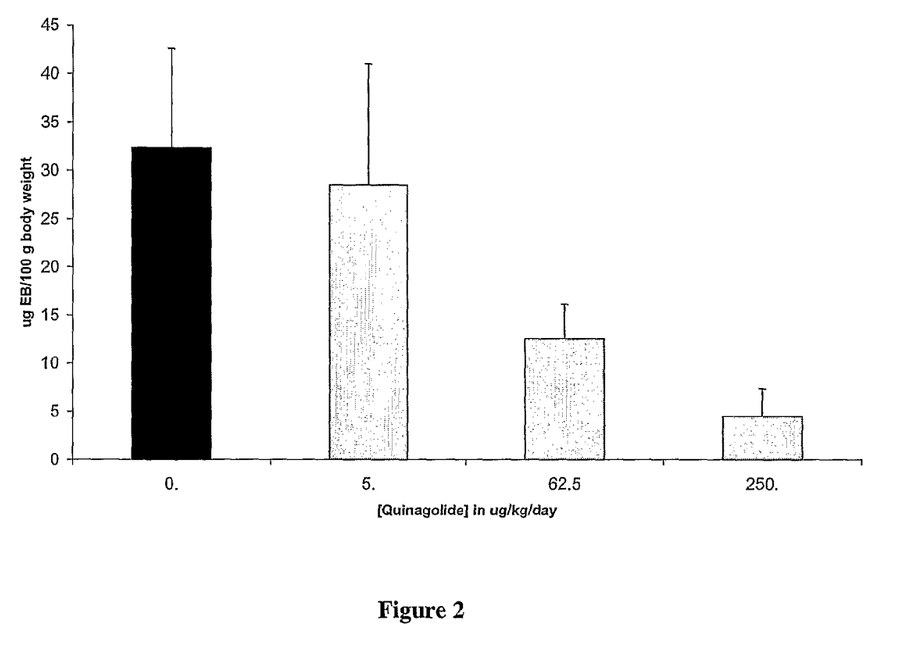
FIG. 2 is a graph depicting the results of a second on the effect of quinagolide on VP in OHSS rats. Vascular Permeability is expressed as µg extravasated Evans Blue dye per 100 g body weight in each animal.

Vascular Permeability is expressed as μg extravasated Evans Blue dye per 100 g body weight in each animal. The raw data from Table 2, above, were used to generate the results depicted in graphic form in FIG. 2. The results presented in FIG. 2 represent the average of the results for the vehicle controls (no quinagolide), positive controls (cabergoline), and for each of the administered amounts of quinagolide (5, 50, and 250 μg/kg body weight), in each rat so tested.

Example 6

The Dopamine Agonist Cabergoline Prevents Moderate-Severe Early Ovarian Hyperstimulation Syndrome (OHSS) in High-Risk ART Patients OHSS has been prevented and treated empirically over the years because its pathophysiology remained unknown. Employing animal models, it has been shown that increased vascular permeability (VP), a hallmark of OHSS, is associated with increased ovarian expression of vascular endothelial growth factor (VEGF) and its receptor 2 (VEGFR2). Binding of VEGF to VEGFR2 disrupts cellular junctions and increases VP. Moreover, employing an antibody specific to VEGFR2, VP induced by gonadotropins has been reversed. However, most of the antiangiogenic molecules able to block VEGFR2 have severe side effects. Dopamine and its agonists also reverse increased VP in hyperstimulated animals by inhibition of VEGFR2 phosphorylation. Based on these observations, Example 6 was performed to determine if the administration of the dopamine receptor-2 agonist cabergoline could prevent OHSS in women at risk undergoing ovarian stimulation for ART.

Materials and Methods. Example 5 is a prospective, randomized and double blind study of 54 oocyte donors in whom 20-30 follicles greater than 12 mm developed, and from whom more than 20 oocytes were retrieved. Immediately after hCG administration, patients were divided in two groups based on a computer randomization: 1) the study group (n=29) received 0.5 mg oral cabergoline daily for eight days; the control group (n=25) received one tablet of placebo for the same eight days. The patients were monitored every 48 hours from the day of hCG administration (day 0) up through day 8. The presence of ascites was defined as a pocket of peritoneal fluid greater than 9 cm$^2$, with the patient in litotomy position seen on vaginal ultrasound. Also, regular blood parameters and serum PRL levels were recorded.

Results: Serum PRL levels were significantly lower (p<0.0001) in the study group on days 2, 4, 6 and 8 as compared to controls. As Table 3, below, shows that haemoconcentration and the presence and volume of ascitic fluid were significantly reduced in the study group.

TABLE 3

|  | Cabergoline group | Control group | p-value |
|---|---|---|---|
| Age* | 24.3 ± 4.1 | 23.4 ± 4.3 | 0.47 |
| Oestradiol (pcg/mL) | 3181.5 ± 1296.3 | 3098.1 ± 786.1 | 0.77 |
| Hematocrit day 4 (%) | 38 6 ± 3.8 | 40.8 ± 2.4 | 0.01 |
| Hematocrit day 6 (%) | 38.9 ± 3.9 | 40.8 ± 2.3 | 0.04 |
| Haemoglobin day 4 (g/dL) | 12.7 ± 1.2 | 13.5 ± 0.8 | 0.006 |
| Haemoglobin day 6 (g/dL) | 12.9 ± 1.2 | 13.6 ± 0.6 | 0.01 |
| Free fluid area day 6 (cm2) | 8.8 ± 1.7 | 17.0 ± 3.2 | 0.03 |
| Ascites % | 24.1 7/29 | 52.0(13/25) | 0.01 |

*Values expressed as mean ± SEM

Conclusions. Cabergoline reduces haemoconcentration and ascites formation in women at risk of developing moderate-severe early OHSS.

What is claimed is:

1. A method for reducing development of ovarian hyperstimulation syndrome (OHSS) in a subject undergoing treatment with a gonadotropin hormone and who is not suffering from polycystic ovary syndrome (PCOS), wherein said method comprises administering, to the subject, an amount of quinagolide effective for reducing vascular permeability.

2. The method of claim 1, wherein the amount of quinagolide does not inhibit angiogenesis in the subject.

3. The method of claim 1, wherein the subject is undergoing infertility treatment.

4. The method of claim 1, wherein the gonadotropin hormone is human chorionic gonadotropin (hCG).

5. The method of claim 3, wherein the infertility treatment is selected from the group consisting of in vitro fertilization (IVF), intracytoplasmic sperm injection (ICSI), gamete intrafallopian transfer (GIFT), zygote intrafallopian transfer (ZIFT) and intrauterine insemination during controlled ovarian stimulation or ovulation induction.

6. The method of claim 1, which comprises administering quinagolide in a dosage range between about 0.025 to about 0.6 mg/day.

7. The method of claim 1, which comprises administering quinagolide in a dosage range between about 0.05 to about 0.3 mg/day.

8. The method of claim 4, which comprises administering quinagolide beginning on the day of administration of human chorionic gonadotropin (hCG).

9. The method of claim 8, which comprises administering quinagolide for at least about 6 to about 8 days after administration of human chorionic gonadotropin.

10. The method of claim 8, which comprises administering quinagolide for between about 5 to about 48 days after administration of human chorionic gonadotropin.

11. The method of claim 8, which comprises administering quinagolide for between about 7 to about 28 days after administration of human chorionic gonadotropin.

12. The method of claim 6, which comprises administering quinagolide prior to triggering final ovulation by administering human chorionic gonadotropin.

13. The method of claim 12, which comprises administering quinagolide for between about 5 to about 48 days after commencing administration of gonadotropin for ovarian stimulation.

14. The method of claim 12, which comprises administering quinagolide for between about 7 to about 28 days after commencing administration of gonadotropin for ovarian stimulation.

15. A method for treating ovarian hyperstimulation syndrome in a subject, which method comprises administering, to a subject in need thereof, and who is not suffering from polycystic ovary syndrome (PCOS), an amount of quinagolide effective for reducing vascular permeability.

16. The method of claim 15, wherein the amount of quinagolide does not inhibit angiogenesis in the subject.

17. The method of claim 15, wherein the ovarian hyperstimulation syndrome is associated with administration of gonadotropin hormone.

18. The method of claim 15, wherein the ovarian hyperstimulation syndrome is idiopathic.

19. The method of claim 15, wherein the ovarian hyperstimulation syndrome is associated with pregnancy.

20. The method of claim 16, wherein the ovarian hyperstimulation syndrome is mild to severe.

21. The method of claim 20, wherein the ovarian hyperstimulation syndrome is severe and the subject is hospitalized.

22. The method of claim 15, which comprises administering quinagolide at a dose of between about 0.025 mg/day to about 0.6 mg/day.

23. The method of claim 15, which comprises administering quinagolide at a dose of between about 0.05 mg/day to about 0.3 mg/day.

24. The method of claim 22, which comprises administering quinagolide for between about 1 day to about 28 days.

25. The method of claim 22, which comprises administering quinagolide for between about 7 days to about 14 days.

* * * * *